(12) United States Patent
De La Torre-Bueno

(10) Patent No.: US 7,505,614 B1
(45) Date of Patent: Mar. 17, 2009

(54) REMOTE INTERPRETATION OF MEDICAL IMAGES

(75) Inventor: Jose De La Torre-Bueno, Encinitas, CA (US)

(73) Assignee: Carl Zeiss MicroImaging AIS, Inc., Thornwood, NY (US)

(*) Notice: Subject to any disclaimer, the term of this patent is extended or adjusted under 35 U.S.C. 154(b) by 0 days.

(21) Appl. No.: 09/542,091

(22) Filed: Apr. 3, 2000

(51) Int. Cl.
*G06K 9/00* (2006.01)
*G06K 9/36* (2006.01)
*G06K 9/46* (2006.01)

(52) U.S. Cl. .............. 382/128; 382/235; 600/437; 709/219

(58) Field of Classification Search ............ 382/128, 382/130, 131, 132, 235; 600/437; 709/219
See application file for complete search history.

(56) References Cited

U.S. PATENT DOCUMENTS

| | | | |
|---|---|---|---|
| 5,428,690 A | | 6/1995 | Bacus et al. |
| 5,432,871 A | * | 7/1995 | Novik ............... 348/14.13 |
| 5,469,353 A | * | 11/1995 | Pinsky et al. ........... 382/131 |
| 5,586,160 A | * | 12/1996 | Mascio ............... 378/37 |
| 5,646,677 A | * | 7/1997 | Reber ............... 348/117 |
| 5,737,446 A | | 4/1998 | Burns |
| 5,740,267 A | * | 4/1998 | Echerer et al. ........... 382/132 |
| 5,851,186 A | * | 12/1998 | Wood et al. ............. 600/437 |
| 5,854,851 A | * | 12/1998 | Bamberger et al. ........ 382/132 |
| 5,966,465 A | * | 10/1999 | Keith et al. ............. 382/232 |
| 6,006,191 A | * | 12/1999 | DiRienzo ............... 705/2 |
| 6,031,929 A | * | 2/2000 | Maitz et al. ............. 382/132 |
| 6,058,322 A | * | 5/2000 | Nishikawa et al. ........ 600/408 |
| 6,101,265 A | * | 8/2000 | Bacus et al. ............. 382/133 |
| 6,115,486 A | * | 9/2000 | Cantoni ............... 382/128 |
| 6,125,194 A | * | 9/2000 | Yeh et al. ............... 382/132 |
| 6,226,392 B1 | * | 5/2001 | Bacus et al. ............. 382/128 |
| 6,226,636 B1 | * | 5/2001 | Abdel-Mottaleb et al. ..... 707/4 |
| 6,261,103 B1 | * | 7/2001 | Stephens et al. ........... 434/276 |
| 6,281,874 B1 | * | 8/2001 | Sivan et al. ............. 345/127 |

(Continued)

FOREIGN PATENT DOCUMENTS

JP 93-080834 4/1991

(Continued)

OTHER PUBLICATIONS

Wallace, The JPEG Still Picture Compression Standard, IEEE Transactions on Consumer Electronics, vol. 38, No. 1, Feb. 1992, p. xxiii.*

*Primary Examiner*—Aaron W Carter
(74) *Attorney, Agent, or Firm*—Patterson, Thuente, Skaar & Christensen, P.A.

(57) ABSTRACT

A remote view station is communicatively coupled to an image server and receives a compressed version of source medical images. The remote view station uncompresses and displays the received medical image. A medical professional, such as a pathologist, can select a region of the displayed medical image. Region information is transmitted back to the image server that applies image analysis operations on a region of the source medical image that corresponds to the selected region of the compressed medical image. In this manner, the data loss that occurs during image compression does not effect the image analysis operations. As such, the image analysis operations produce more accurate results than if the operations were applied by remote view station to the uncompressed image.

13 Claims, 3 Drawing Sheets

U.S. PATENT DOCUMENTS

| | | | |
|---|---|---|---|
| 6,314,452 B1 | 11/2001 | Dekel et al. | |
| 6,404,906 B2 * | 6/2002 | Bacus et al. | 382/128 |
| 6,621,918 B1 * | 9/2003 | Hu et al. | 382/128 |
| 6,778,709 B1 | 8/2004 | Taubman | |
| 7,110,586 B2 * | 9/2006 | Bacus et al. | 382/128 |
| 7,146,372 B2 * | 12/2006 | Bacus et al. | 707/100 |
| 2002/0061127 A1 * | 5/2002 | Bacus et al. | 382/128 |

FOREIGN PATENT DOCUMENTS

| | | |
|---|---|---|
| JP | 09-117417 | 5/1997 |
| JP | 09-200756 | 7/1997 |

\* cited by examiner

REMOTE INTERPRETATION OF MEDICAL IMAGES

BACKGROUND

Pathologists typically use microscopes when diagnosing physiological conditions such as cancer, infectious disease and prenatal disorders. Typically, tissue samples on a slide are loaded onto the microscope, the microscope objective or lens focuses on an area of the sample, and the sample is scanned for particular features or objects of interest. In this manner, the microscope helps the pathologist to visually determine the presence of abnormal numbers or types of cells, organelles, organisms or biological markers.

Recently, automated microscopes have been integrated into medical imaging systems that include a variety of networked components. The medical imaging system provides an environment for storing and retrieving the medical images produced by the microscopes. The components of the medical imaging system are spread throughout the department or hospital, or even located remotely, and connected by a communication network.

An image acquisition device is coupled to the microscope and captures images produced by the microscope. The image acquisition device can include a variety of components. For example, the image acquisition device can include a video camera coupled to a high-speed frame grabber for capturing the stream of video produced by the video camera and generating a series of digital images. Alternatively, the electronic camera can be a megapixel digital camera. The microscope and the image acquisition device can acquire images for a number of different color planes and at several different focal planes. These images can be stitched together to form a two-dimensional or three-dimensional composite image. As a result of the combination, and because the images are typically in color and at high-resolution, the composite images place significant storage and bandwidth requirements on the medical imaging system. For example, a composite image for a single tissue slide can often exceed a gigabyte in size.

Image storage and archival devices provide a central library for storing the medical images captured by the image acquisition device. Image storage devices include one or more databases and image servers for fast access to recently acquired images. Archival devices, such as optical disc jukeboxes and tape backup systems, provide long-term storage. When a pathologist wishes to view an archived image, the image is automatically "migrated" from the corresponding archival device to one of the image storage devices.

Diagnostic quality view stations display the images captured by the image acquisition system. In order to assist the pathologist in interpreting a medical image, a view station is able to perform a variety of image processing operations on the medical image. For example, the pathologist at the view stations may invoke algorithms to perform densitometry on selected regions of the medical image in order to identify concentration of a particular analyte within the tissue sample. Other image processing operations are useful for finding objects within the image such as the nuclei of the cells, computing an integrated optical density for the nuclei of the cells and reporting the number of molecules per cell. Most image processing operations output a fixed number (score), often falling within a predetermined range.

SUMMARY OF THE INVENTION

In general, the invention facilitates the remote interpretation of medical images. In order to facilitate the timely diagnosis of a tissue sample, it is desirable that a medical professional, such as a pathologist, be able to remotely view and interpret a medical image. The immense size of a medical image for a single tissue sample typically makes remote viewing unworkable due to bandwidth constraints. Compression algorithms can produce an image suitable for transmission, but the data lost during compression can lead to inaccurate results from the image analysis operations.

According to one aspect, the invention is directed to a system in which a remote view station is communicatively coupled to an image server and receives a compressed version of a source medical image. The remote view station uncompresses and displays the received medical image. The remote view station selects a region of the displayed medical image as a function of input received from a medical professional, such as a pathologist. Based on the input, the remote view station transmits region information, such as a series of pixel coordinates, back to the image server. The image server applies image analysis operations to a region of the source medical image that corresponds to the selected region of the compressed medical image. In this manner, the data loss that occurs during image compression does not effect the image analysis operations. As such, the image analysis operations produce more accurate results than if the operations were applied by the remote view station on the compressed image.

In another aspect, the invention is directed to a method for remotely interpreting medical images. According to the method, a compressed medical image is generated from a source medical image and transmitted from an image server to a remote view station for display. In one implementation, the compressed medical image is transmitted over a global packet-switched network such as the Internet. A region of the medical image displayed by the remote view station is selected in response to input from a medical professional. Region information, defining the selected region of the displayed medial image, is transmitted from the remote view station back to the image server. Based on the region information, image analysis operations are applied to a corresponding region of the source medical image. A resulting score is communicated to the remote view station for display. A diagnosis is received from the remote view station and associated with the source medical image in a database maintained by the image server.

Various embodiments of the invention are set forth in the accompanying drawings and the description below. Other features and advantages of the invention will become apparent from the description, the drawings, and the claims.

DETAILED DESCRIPTION

Figure 1:
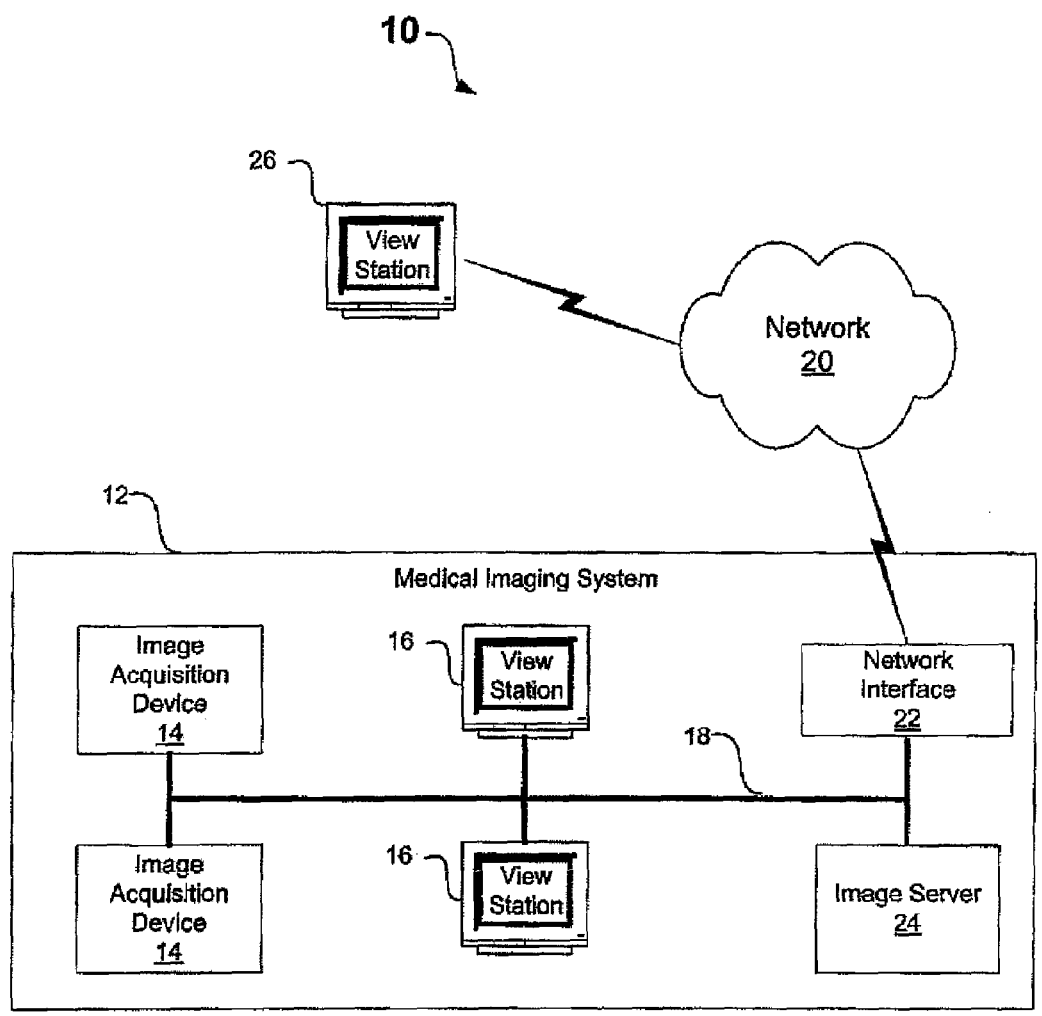
FIG. 1 is a block diagram providing a high-level illustration of the various components of the invention.

FIG. 1 is a block diagram illustrating a system 10 that facilitates remotely viewing and interpreting medical images. System 10 includes remote view station 26 this is communicatively coupled to medical imaging system (MIS) 12 by network 20, which represents any packet-switched network such as a local area network or the Internet. MIS 12 includes image acquisition devices 14 that represent any medical imaging device that generates digital medical images, such as an electronic camera used in conjunction with an automated microscope. Other image acquisition devices include computed tomography (CT), nuclear medicine, magnetic resonance imaging (MRI), ultrasound and X-ray devices. Image server 24 stores the images that are generated by image acquisition device 14 and, upon request, communicates the images to view stations 16 for display. Using view stations 16, a medical professional, such as a pathologist, can perform a variety of image processing techniques on selected regions to assist in rendering a diagnosis.

As described in detail below, image server 24 of MIS 12 communicates compressed medical images to remote view station 26 for interpretation by a medical professional. Using a network software application, such as a web browser, the medical professional interacts with remote view station 26 to select various regions of interest within the image. Based on the selection, image server 24 applies image analysis functions directly to the source medical image stored on image server 24, thereby generating a more accurate score than if applied by remote view station 26 to the medical image after compression. The resultant score produced by the image processing operations is communicated to remote view station 26 to assist the medical professional in interpreting the medical image and rendering a diagnosis.

Figure 2:
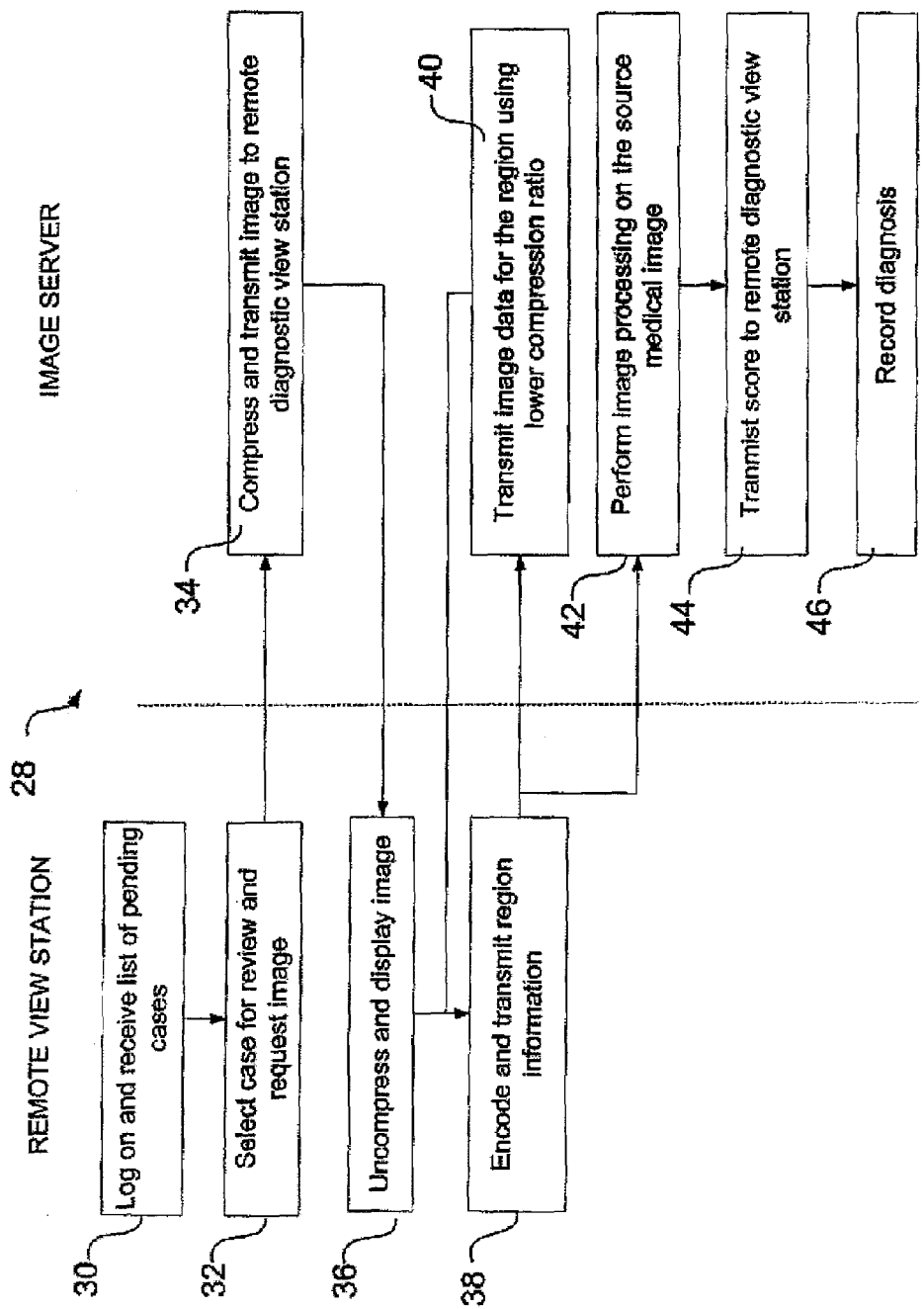
FIG. 2 is a flowchart illustrating one embodiment of a process for remotely interpreting medical images.

FIG. 2 is a flow chart illustrating one implementation of a process 28 that facilitates the interpretation of medical images via remote view station 26. Using a network software application the medical professional interacts with remote view station 26, accesses MIS 12 and receives a list of cases that are marked for review, i.e., cases in which images have been acquired by image acquisition devices 14 but have not been reviewed by a medical professional (30). Upon reviewing the list displayed by remote view station 26, the medical professional selects one of the cases for review (32).

Based on the selection, image server 24 compresses medical images associated with the case and communicates the compressed images to remote view station 26 via network 20 (34). Remote view station 26 decompresses the images and displays the uncompressed images for review by the medical professional (36). The displayed image is not a pixel-by-pixel duplicate of the original source image stored on image server 24 because of data lossed during compression. Several algorithms, however, are known that can achieve a compression ratio, such that the compressed image uses relatively low bandwidth, without significantly changing the visual representation of the image. Therefore, compressing the image can be effectively lossless with respect to human vision. For example, it has been found that both JPEG compression and fractal image compression, when set for moderate compression, result in images suitable for transmission without resulting in data loss perceptible with human vision.

Using a pointing device, such as a light pen, mouse or track ball, the medical professional selects one or more regions of interest. The medical professional can tag a region for image processing or can request that image server 24 transmit image data for the selected region using a lower compression setting. For example, the medical professional can direct image server 24 to transmit an image using low compression or even to transmit an uncompressed pixel-by-pixel duplicate of the selected region. Remote view station 26 encodes the shape and size of the selected region and transmits the region information to MIS 12 by network 20 (38). The region information defines the boundaries of the selected regions and, in one implementation, is a set of pixel coordinates defining the outlines of the selected regions. As such, the region information typically comprises a small amount information and can be quickly transmitted to image server 24.

If the medical professional requests that image server 24 transmit image data for a region of interest using a lower compression setting, or no compression, then image server 24 extracts the corresponding pixel data from the source image and communicates the pixel data to remote view station 26 (40). In this fashion, the medical professional can view regions of interest at higher resolution, or even a pixel-per-pixel duplicate, without requiring that image server 24 transmit the entire source image across network 20. Upon viewing the region of interest, the medical professional can tag the region for image processing or can select sub-regions of interest.

If the medical professional tags a selected region for image processing, image server 24 executes the requested image processing operation on the corresponding source medical image (42). More specifically, image server 24 analyzes the region information received from remote view station 26 and applies the image processing operation to a subset of the pixel data of the source image. The subset pixel data is selected based on the boundaries defined by the region information received from remote view station 26. In this manner, the image processing operation produces a more accurate score than if the operation were applied by remote view station 26 to the image that has been compressed for transmission and then uncompressed for display at the remote view station. As such, the data loss that occurs during compression does not effect the image analysis.

Image server 24 communicates the scores for each region to remote view station 26 for display to the medical professional (44). Based on the visual display of the medical image as well as the scores associated with regions of interest, the medical professional interprets the medical image and renders a diagnosis. For example, the medical professional may determine that a particular tissue sample is cancerous. Remote view station 26 communicates the diagnosis to MIS 12 for association with the appropriate case within a database maintained by image server 24 (46).

The invention can be implemented in digital electronic circuitry, or in computer hardware, firmware, software, or in combinations thereof. Furthermore, the invention can be implemented in one or more computer programs that are executable within an operating environment of a programmable system embodied and tangibly stored in a machine-readable storage device.

Figure 3:
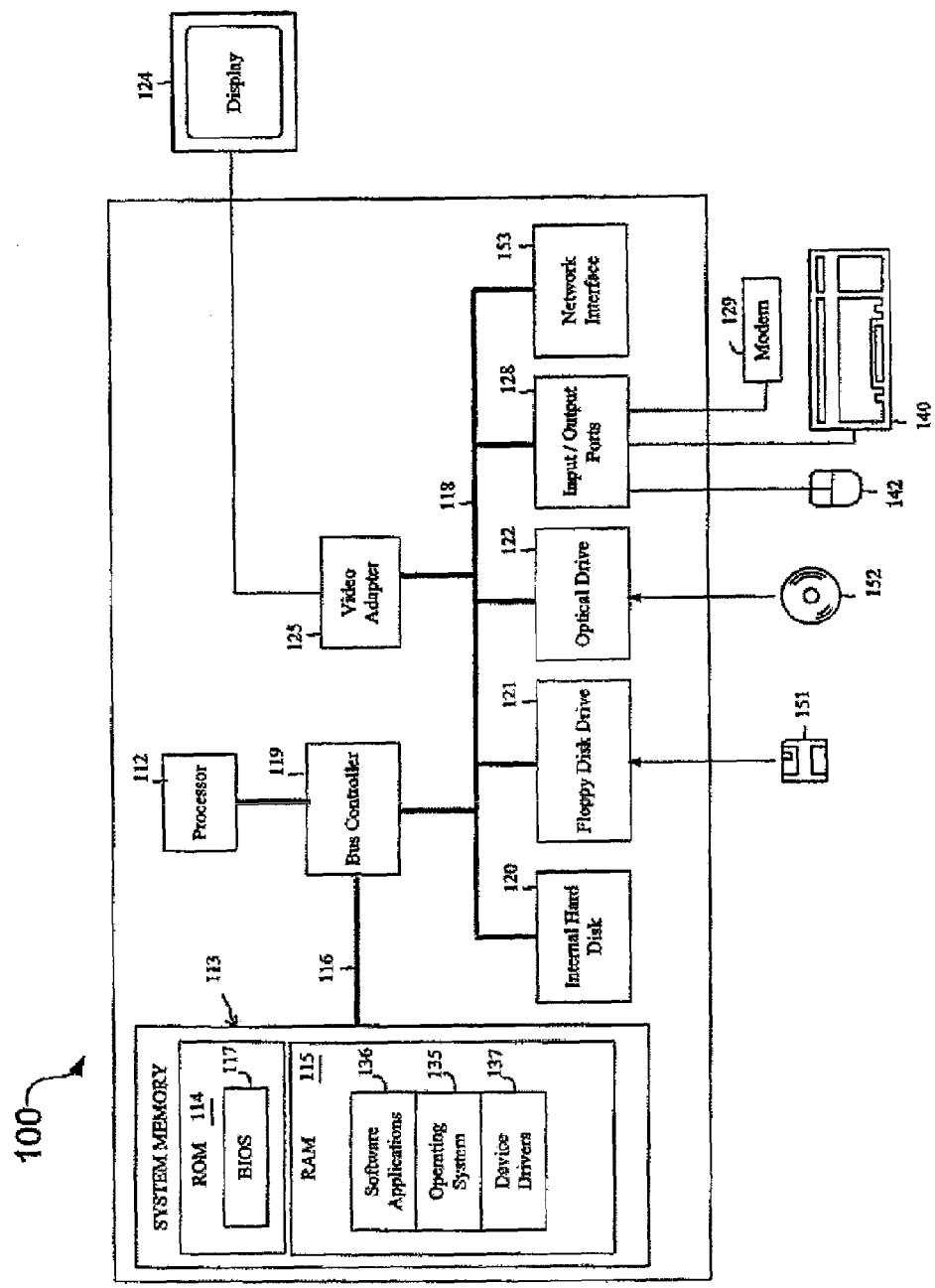
FIG. 3 is a block diagram illustrates one embodiment of a computer suitable for implementing the various embodiments of the invention.

FIG. 3 illustrates an example of a computer 100 suitable for use as view station 26 in order to implement or perform various embodiments of the invention. As shown in FIG. 3, the computer 100 includes a processor 112 that in one embodiment belongs to the PENTIUM® family of microprocessors manufactured by the Intel Corporation of Santa Clara, Calif. However, computer 100 can be implemented on computers based upon other microprocessors, such as the MIPS® family of microprocessors from the Silicon Graphics Corporation, the POWERPC® family of microprocessors from both the Motorola Corporation and the IBM Corporation, the PRECISION ARCHITECTURE® family of microprocessors from the Hewlett-Packard Company, the SPARC® family of microprocessors from the Sun Microsystems Corporation, or the ALPHA® family of microprocessors from the Compaq Computer Corporation.

Computer 100 includes system memory 113, including read only memory (ROM) 114 and random access memory (RAM) 115, which is connected to the processor 112 by a system data/address bus 116. ROM 114 represents any device that is primarily read-only including electrically erasable programmable read-only memory (EEPROM), flash memory, etc. RAM 115 represents any random access memory such as Synchronous Dynamic Random Access Memory.

Within the computer 100, input/output bus 118 is connected to the data/address bus 116 via bus controller 119. In one embodiment, input/output bus 118 is implemented as a standard Peripheral Component Interconnect (PCI) bus. The bus controller 119 examines all signals from the processor 112 to route the signals to the appropriate bus. Signals between the processor 112 and the system memory 113 are merely passed through the bus controller 119. However, signals from the processor 112 intended for devices other than system memory 113 are routed onto the input/output bus 118.

Various devices are connected to the input/output bus 118 including hard disk drive 120, floppy drive 121 that is used to read floppy disk 151, and optical drive 122, such as a CD-ROM drive that is used to read an optical disk 152. The video display 124 or other kind of display device is connected to the input/output bus 118 via a video adapter 125 and preferably is a high-resolution display suitable for viewing medical images. Computer 100 also includes a modem 129 and network interface 53 for communicating over network 20 via either a wired or wireless connection.

A medical professional enter commands and information into the computer 100 by using a keyboard 140 and/or pointing device, such as a mouse 142, which are connected to bus 118 via input/output ports 128. Other types of pointing devices (not shown in FIG. 1) include track pads, track balls, joysticks, data gloves, head trackers, and other devices suitable for positioning a cursor on the video display 124.

Software applications 136 and data are typically stored via one of the memory storage devices, which may include the hard disk 120, floppy disk 151, CD-ROM 152 and are copied to RAM 115 for execution. Operating system 135 executes software applications 136 and carries out instructions issued by the user. The Basic Input/Output System (BIOS) 117 for the computer 100 is stored in ROM 114 and is loaded into RAM 115 upon booting. BIOS 117 is a set of basic executable routines that help transfer information between the computing resources within the computer 100.

This application is intended to cover any adaptation or variation of the present invention. It is intended that this invention be limited only by the claims and equivalents thereof.

What is claimed is:

1. A method, comprising:
   obtaining, at a first location, an original medical image representing medical information to be evaluated by an evaluating person;
   compressing the original medical image to form a compressed medical image, at the first location;
   sending the compressed medical image from the first location to a second location, at which second location the evaluating person is located;
   allowing selection of a region of the compressed medical image at the second location, which region is less than the entire compressed medical image, and sending an indication of that region to the first location; and
   carrying out a medical analysis of only the region of the medical image at said first location, said medical analysis being based on the contents of the original medical image that are within the region selected by the evaluating person.

2. The method of claim 1, wherein said sending the compressed medical image includes transmitting the compressed medical image over a global packet-switched network.

3. The method of claim 1 wherein said second location includes a remote view station and further including transmitting said indication from the remote view station to an image server, wherein the region information defines the selected region of the displayed medical image.

4. The method of claim 3, wherein the indicator is transmitted as a series of pixel coordinates.

5. The method of claim 1, wherein said allowing selection selecting the region of the compressed medical image includes receiving input from a pointing device controlled by a user to outline the region of the compressed medical image.

6. A system comprising:
   an image server, at a first location, obtaining an original medical image representing medical information to be evaluated by an evaluating person;
   said image server including an image compression part which compresses the image to form a compressed medical image, and including a network communicating part which communicates the compressed medical image over a network;
   a remote view station at a second location, including a network communicating part receiving said compressed medical image, a viewing part enabling said image to be viewed, and enabling a region of said image to be selected, where information indicative of said region is sent back to the image server; and
   wherein the image server also includes a medical analysis part at said first location, which enables carrying out a medical analysis of only the region of the medical image, based on the contents of the original medical image, that are within the region that was selected.

7. The system of claim 6, wherein the remote view station transmits region information separate from the compressed medical image from the remote view station to the imaged server, wherein the region information-includes a plurality of pixel coordinates outlining the selected region the compressed image.

8. The system of claim 6, wherein the image server applies the image analysis operations to generate a score and communicate the score to the remote view station for display.

9. The system of claim 6, wherein the image server includes a database associating a diagnosis received from the remote view station with the source medical image.

10. The system of claim 6, wherein the remote view station includes a pointing device controllable by a user to outline the region of the compressed medical image.

11. The system as in claim 8, wherein said medical analysis part is a computer which automatically processes the original medical image to calculate said score.

12. The system as in claim 1, wherein said carrying out a medical analysis comprises using the computer to automatically process the original medical image at its original location.

13. The system as in claim 12, wherein said carrying out a medical analysis comprises automatically forming a score indicative of the image, and sending said score to the second location.

* * * * *